(12) United States Patent
Bauco et al.

(10) Patent No.: US 10,856,952 B2
(45) Date of Patent: *Dec. 8, 2020

(54) MEDICAL DEVICE DISINFECTING SYSTEM AND METHOD

(71) Applicant: CORNING INCORPORATED, Corning, NY (US)

(72) Inventors: Anthony Sebastian Bauco, Horseheads, NY (US); Kevin Wallace Bennett, Hammondsport, NY (US); William Spencer Klubben, III, Boston, MA (US); Horst Schreiber, Livonia, NY (US)

(73) Assignee: CORNING INCORPORATED, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/715,327

(22) Filed: Dec. 16, 2019

(65) Prior Publication Data

US 2020/0138545 A1 May 7, 2020

Related U.S. Application Data

(63) Continuation of application No. 15/753,824, filed as application No. PCT/US2016/047490 on Aug. 18, 2016, now Pat. No. 10,543,058.

(Continued)

(51) Int. Cl.
*A61B 90/70* (2016.01)
*A61L 2/10* (2006.01)
(Continued)

(52) U.S. Cl.
CPC .............. *A61B 90/70* (2016.02); *A61L 2/084* (2013.01); *A61L 2/10* (2013.01); *G02B 6/001* (2013.01);
(Continued)

(58) Field of Classification Search
CPC ...... A61L 2202/24; A61L 2/10; A61L 2/0047; A61L 2/00; A61L 2/08; A61L 2202/14;
(Continued)

(56) References Cited

U.S. PATENT DOCUMENTS 4,579,597 A 4/1986 Sasa et al.
5,637,877 A 6/1997 Sinofsky
(Continued)

FOREIGN PATENT DOCUMENTS

CN 204840698 U 12/2015
CN 106178280 A 12/2016
(Continued)

OTHER PUBLICATIONS

Author Unknown; "Study Shows Effectiveness of Ultraviolet Light in Hospital Infection Control"; Oct. 25, 2012; 4 Pages; http://www.infectioncontroltoday.com/news/2012/10/study-shows-effectiveness-of-ultraviolet-light-in-hospital-infection-control.aspx.
(Continued)

*Primary Examiner* — David A Vanore

(57) ABSTRACT

A system for disinfecting a medical device is provided. The system includes a light source that generates light having at least one wavelength between about 100 nm and about 500 nm. The system further includes at least one cylindrical optical diffuser disposed in optical communication with at least one interior channel of a medical device, the at least one cylindrical optical diffuser having an outer surface and an end optically coupled to the light source. The at least one cylindrical optical diffuser is configured to scatter guided light through the outer surface to form a light diffuser portion having a length that emits substantially uniform radiation over its length.

39 Claims, 5 Drawing Sheets

Related U.S. Application Data

(60) Provisional application No. 62/278,197, filed on Jan. 13, 2016, provisional application No. 62/208,239, filed on Aug. 21, 2015.

(51) Int. Cl.
*A61L 2/08* (2006.01)
*F21V 8/00* (2006.01)
*G02B 6/02* (2006.01)

(52) U.S. Cl.
CPC ...... *G02B 6/0229* (2013.01); *A61B 2090/701* (2016.02); *A61L 2202/24* (2013.01)

(58) Field of Classification Search
CPC ......... A61L 2/0029; A61M 2025/0019; A61M 16/04; A61M 2205/053; A61N 5/0624; A61N 5/0601; A61N 2005/0661; A61B 1/07; A61B 1/0653; A61B 2018/2261; A61B 2090/306; A61B 90/30; G02B 6/00; G02B 6/02333; G02B 6/102
USPC ......... 250/492.1, 372, 431, 453.11; 385/123, 385/125; 362/554
See application file for complete search history.

(56) References Cited

U.S. PATENT DOCUMENTS

| | | | |
|---|---|---|---|
| 6,551,346 B2 | 4/2003 | Crossley | |
| 7,175,806 B2 | 2/2007 | Deal et al. | |
| 7,291,308 B2 | 11/2007 | Wu et al. | |
| 8,404,273 B2 | 3/2013 | Baumgart et al. | |
| 8,444,930 B2 | 5/2013 | Komiya et al. | |
| 8,490,235 B2 | 7/2013 | Soetermans | |
| 8,585,681 B2 | 11/2013 | Boenig et al. | |
| 8,623,275 B2 | 1/2014 | Deshays | |
| 8,779,386 B2 | 7/2014 | Bak | |
| 8,840,733 B2 | 9/2014 | Komiya et al. | |
| 8,980,174 B2 | 3/2015 | Haytman et al. | |
| 9,039,966 B2 | 5/2015 | Anderson et al. | |
| 9,067,059 B2 | 6/2015 | Bissig et al. | |
| 9,259,513 B2 | 2/2016 | Bedwell et al. | |
| 9,393,339 B2 | 7/2016 | Park et al. | |
| 9,439,989 B2 | 9/2016 | Lalicki et al. | |
| 9,550,005 B2 | 1/2017 | Lin et al. | |
| 9,748,522 B2 | 8/2017 | Verschuren et al. | |
| 9,795,466 B2 | 10/2017 | Piergallini et al. | |
| 9,808,647 B2 | 11/2017 | Rhodes et al. | |
| 9,872,978 B1 | 1/2018 | Zaborsky et al. | |
| 9,925,390 B2 | 3/2018 | Yehezkel | |
| 9,943,379 B2 | 4/2018 | Gregg, II et al. | |
| 10,046,070 B1 | 8/2018 | Zaborsky et al. | |
| 10,166,402 B2 | 1/2019 | Brennan et al. | |
| 10,183,144 B2 | 1/2019 | Tang et al. | |
| 10,241,035 B2 | 3/2019 | Bonnick et al. | |
| 10,543,058 B2 * | 1/2020 | Bauco | A61L 2/10 |
| 2006/0085052 A1 | 4/2006 | Feuerstein et al. | |
| 2007/0104437 A1 | 5/2007 | Bookbinder et al. | |
| 2009/0257910 A1 | 10/2009 | Segal | |
| 2010/0268151 A1 | 10/2010 | Mauge et al. | |
| 2011/0122646 A1 | 5/2011 | Bickham et al. | |
| 2012/0118338 A1 | 5/2012 | Nakanishi | |
| 2013/0035629 A1 | 2/2013 | Soltz et al. | |
| 2013/0060188 A1 | 3/2013 | Bedwell et al. | |
| 2013/0267888 A1 | 10/2013 | Rhodes et al. | |
| 2013/0270445 A1 | 10/2013 | Gaska et al. | |
| 2014/0134071 A1 | 5/2014 | Suzuki et al. | |
| 2014/0271348 A1 | 9/2014 | Deal et al. | |
| 2015/0080709 A1 | 3/2015 | Chaturvedi | |
| 2015/0126976 A1 | 5/2015 | Tang et al. | |
| 2015/0231287 A1 | 8/2015 | Lin et al. | |
| 2017/0224952 A1 | 8/2017 | Barneck et al. | |
| 2018/0015302 A1 | 1/2018 | Barneck et al. | |
| 2018/0036443 A1 | 2/2018 | Messerly | |
| 2018/0064322 A1 | 3/2018 | Klubben, III et al. | |
| 2018/0147417 A1 | 5/2018 | Rantala | |
| 2018/0178031 A1 | 6/2018 | Wu | |
| 2018/0207302 A1 | 7/2018 | Vasilenko | |
| 2018/0304094 A1 | 10/2018 | Hicks et al. | |
| 2018/0326104 A1 | 11/2018 | Hawkins et al. | |
| 2018/0369432 A1 | 12/2018 | Zaborsky | |

FOREIGN PATENT DOCUMENTS

| | | |
|---|---|---|
| CN | 106178282 A | 12/2016 |
| CN | 105396169 B | 6/2018 |
| CN | 108671243 A | 10/2018 |
| JP | 05546575 B2 | 7/2014 |
| KR | 1362704 B1 | 2/2014 |
| KR | 1851576 B1 | 4/2018 |
| KR | 2018049757 A | 5/2018 |
| KR | 1892996 B1 | 8/2018 |
| KR | 2018135256 A | 12/2018 |
| KR | 2018135257 A | 12/2018 |
| TW | 201041610 A | 12/2010 |
| WO | 2014159874 A1 | 10/2014 |
| WO | 2015168129 A1 | 11/2015 |
| WO | 2016154186 A1 | 9/2016 |
| WO | 2018009864 A1 | 1/2018 |
| WO | 2019025808 A1 | 2/2019 |

OTHER PUBLICATIONS

Eisler; "Deadly Bacteria on Medical Scopes Trigger Infections"; Jan. 21, 2015; 6 Pages; http://www.usatoday.com/story/news/2015/01/21/bacteria-deadly-endoscope-contamination/22119329/.

International Search Report and Written Opinion of the International Searching Authority; PCT/US2016/047490; dated Nov. 18, 2016; 13 Pages; European Patent Office.

Spach et al; "Transmission of Infection by Gastrointestinal Endoscopy and Brochoscopy"; Annals of Internal Medicine, 118; (1993); pp. 117-128.

TW105126491 Office Action dated Apr. 17, 2020; 3 Pages; Taiwan Patent Office.

Chinese Patent Application No. 20160057446.5; English Translation of the Office Action dated Feb. 10, 2020; China Patent Office; 8 Pgs.

* cited by examiner

MEDICAL DEVICE DISINFECTING SYSTEM AND METHOD

This application is a continuation application and claims the benefit of priority under 35 U.S.C. § 120 of U.S. patent application Ser. No. 15/753,824 filed on Feb. 20, 2018, which is a US 371 of PCT/US2016/047490 filed on Aug. 18, 2016, which claims the benefit of priority under 35 U.S.C. § 119 of U.S. Provisional Application Ser. No. 62/278,197 filed on Jan. 13, 2016 and U.S. Provisional Application Ser. No. 62/208,239 filed on Aug. 21, 2015, the contents of which are relied upon and incorporated herein by reference in their entirety.

FIELD

The present disclosure generally relates to medical devices, medical device disinfecting systems, and disinfection methods. More particularly, the present disclosure relates to medical devices having at least one cylindrical optical diffuser, medical device disinfecting systems including at least one cylindrical optical diffuser, and disinfection methods using at least one cylindrical optical diffuser.

BACKGROUND

Bacteria that exist in health care settings differ significantly from bacteria found in a general community setting, primarily in their resistance to antibiotic therapy. In many ways, the hospital environment contributes to the problem by harboring virulent strains of bacteria, fungi, and viruses. This is at least partly a result of the fact that many conventional disinfection methods are ineffective and may actually spread contaminants. Additionally, when subjected to the methods of disinfection on a regular basis, bacteria develop resistance to the methods over time. These contaminants are present on objects, and in particular, medical devices in the hospital setting. For medical devices that cannot be disposed of after a single use, the devices must be disinfected between uses. Additionally, some medical devices which are placed partially inside the body and partially outside the body for an extended period of time are at an increased risk of infection.

Examples of such medical devices are flexible and rigid endoscopes. Some systems for cleaning such endoscopes are configured to allow the endoscope to be housed in a processing tank to be cleaned and disinfected with the use of liquid detergent and disinfectant solution. However, endoscopes may have a plurality of interior channels or lumens that are difficult to reach and disinfect. Such channels are used to inject liquid irrigants, suction, and to pass flexible surgical instruments such as biopsy forceps.

Some mechanical aids have been developed for use in cleaning the interior channels or lumens of an endoscope. For example, brush devices that fit into interior channels or lumens are equipped with bristles that project from a central shaft to provide mechanical abrasion to the surfaces of the interior channels or lumens of an endoscope. Also, sponge devices that fit into interior channels or lumens spread contamination into a substantially uniform film on the surfaces of the interior channels or lumens of an endoscope so that enzymatic cleaners can more efficiently and uniformly digest the contaminating material. However, the bristles of the brush devices do not provide uniform contact with the surfaces of the interior channels or lumens of an endoscope, and the sponge devices merely spread contaminants and are not configured to provide the mechanical force needed to remove contaminants adhering to surfaces of the interior channels or lumens of an endoscope.

SUMMARY

According to an embodiment of the present disclosure, a system for disinfecting a medical device is provided. The system includes a light source that generates light having at least one wavelength between about 100 nm and about 500 nm. The system further includes at least one cylindrical optical diffuser disposed in optical communication with at least one interior channel of a medical device, the at least one cylindrical optical diffuser having an outer surface and an end optically coupled to the light source. The at least one cylindrical optical diffuser is configured to scatter guided light through the outer surface to form a light diffuser portion having a length that emits substantially uniform radiation over its length.

According to another embodiment of the present disclosure, a medical device is provided. The medical device includes at least one interior channel and at least one cylindrical optical diffuser disposed in optical communication with the least one interior channel, the at least one cylindrical optical diffuser having an outer surface and an end optically coupled to a light source. The at least one cylindrical optical diffuser is configured to scatter guided light through the outer surface to form a light diffuser portion having a length that emits substantially uniform radiation over its length.

According to another embodiment of the present disclosure, a disinfection method is provided. The method includes inserting at least a portion of at least one cylindrical optical diffuser into an interior channel of a medical device and introducing light from a light source into an end of the at least one cylindrical optical diffuser optically coupled to the light source and emitting the light through the outer surface of the diffuser to illuminate a portion of the diffuser and to expose the interior channel to the emitted light. The at least one cylindrical optical diffuser is configured to scatter guided light through the outer surface to form a light diffuser portion having a length that emits substantially uniform radiation over its length, and to disinfect at least one surface of the interior channel.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

The disclosure will be understood more clearly from the following description and from the accompanying figures, given purely by way of non-limiting example, in which.

DETAILED DESCRIPTION

Figure 1:
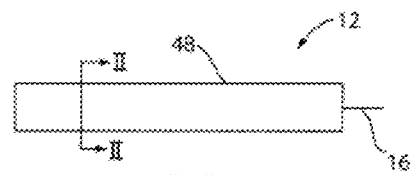
FIG. 1 is a schematic side view of a section of an example embodiment of light-diffusing optical fiber.

Reference will now be made in detail to the present embodiment(s), an example(s) of which is/are illustrated in the accompanying drawings. Whenever possible, the same reference numerals will be used throughout the drawings to refer to the same or like parts.

The singular forms "a," "an" and "the" include plural referents unless the context clearly dictates otherwise. The endpoints of all ranges reciting the same characteristic are independently combinable and inclusive of the recited endpoint. All references are incorporated herein by reference.

Embodiments of the present disclosure relate to medical devices, medical device disinfecting systems, and disinfection methods. Embodiments of the present disclosure include at least one cylindrical optical diffuser that may transmit ultraviolet irradiation, or short wavelength visible light. As used herein, a cylindrical optical diffuser refers to a diffuser that emits light through its outer surface when light is introduced into the diffuser as guided light. While some of the embodiments included herein describe "at least one cylindrical optical diffuser", it should be understood that embodiments including a plurality of cylindrical optical diffusers are also comprehended. As used herein, the term "ultraviolet" (UV) light is used for a wavelength of light being less than about 400 nm, and the term "short wavelength visible light" is used for a wavelength of light being between about 400 nm and about 500 nm. Ultraviolet light, particularly in the C bandwidth, when given in adequate doses is lethal to all known pathogens. As used herein, the term "ultraviolet light in the C bandwidth" (UV-C) is used for a wavelength of light being utilized for its germicidal properties, the wavelength being between about 100 nm and about 290 nm. Additionally, recent studies have shown that short wavelength visible light, such as violet and blue light, is also lethal to bacteria, fungi, and viruses at certain doses. Such short wavelength visible light may be, for example, between about 400 nm and about 450 nm, or between about 405 nm and about 415 nm.

The cylindrical optical diffuser may be, for example, a side-emitting fiber, or a bundle of two or more side-emitting fibers. Side-emitting fibers can be, for example, a single plastic or glass core without any cladding or coating in which light sent into the core is lost through the side surfaces of the fiber because the light is not trapped or internally guided. Side-emitting fiber may include scattering defects introduced into the fiber at various locations, such as by doping the core of the fiber with small refractive and/or reflective light-scattering particles, or by modifying a surface of the core to have surface features that scatter light out of the core. Examples of light-emitting surface defects include serrations, notches, scratches, texture, roughness, corrugations, etching, abrasion, etc. Alternatively, the cylindrical optical diffuser may be a light diffusing optical fiber. As used herein, the term "light diffusing optical fiber" refers to a flexible optical waveguide configured to diffuse light out of the sides of the fiber, such that light is guided away from the core of the waveguide and through the outer surfaces of the waveguide to provide illumination.

Concepts relevant to the underlying principles of the claimed subject matter are disclosed in U.S. Patent Application Publication No. US 2011/0122646 A1, which is incorporated in its entirety herein by reference. As described in greater detail below, exemplary light diffusing optical fiber may include a core, a primary cladding, and a plurality of nano-sized structures situated within the core or at a core-cladding boundary. The optical fiber further includes an outer surface, and an end configured to optically couple to a light source. The light diffusing optical fiber may be configured to scatter guided light via the nano-sized structures away from the core and through the outer surface, to form a light-source fiber portion having a length that emits substantially uniform radiation over its length The term "light source" refers to a laser, light emitting diode or other component capable of emitting electromagnetic radiation that is either in the UV light range of wavelengths or is of a wavelength that can interact with a luminophore to emit light in the UV light range of wavelengths.

The term "luminophore" refers to an atom or chemical compound that manifests luminescence, and includes a variety of fluorophores and phosphors.

The following terms and phrases are used in connection with light diffusing fibers having nano-sized structures.

The "refractive index profile" is the relationship between the refractive index or the relative refractive index and the waveguide (fiber) radius.

The "relative refractive index percent" is defined as $$\Delta(r)\% = 100 \times [n(r)^2 - n_{REF}^2]/2n(r)^2,$$

where n(r) is the refractive index at radius r, unless otherwise specified. The relative refractive index percent is defined at 850 nm unless otherwise specified. In one aspect, the reference index $n_{REF}$ is silica glass with a refractive index of 1.452498 at 850 nm, in another aspect it is the maximum refractive index of the cladding glass at 850 nm. As used herein, the relative refractive index is represented by $\Delta$ and its values are given in units of "%", unless otherwise specified. In cases where the refractive index of a region is less than the reference index $n_{REF}$, the relative index percent is negative and is referred to as having a depressed region or depressed-index, and the minimum relative refractive index is calculated at the point at which the relative index is most negative unless otherwise specified. In cases where the refractive index of a region is greater than the reference index $n_{REF}$, the relative index percent is positive and the region can be said to be raised or to have a positive index.

An "updopant" is herein considered to be a dopant which has a propensity to raise the refractive index relative to pure undoped $SiO_2$. A "downdopant" is herein considered to be a dopant which has a propensity to lower the refractive index relative to pure undoped $SiO_2$. An updopant may be present in a region of an optical fiber having a negative relative refractive index when accompanied by one or more other dopants which are not updopants. Likewise, one or more other dopants which are not updopants may be present in a region of an optical fiber having a positive relative refractive index. A downdopant may be present in a region of an optical fiber having a positive relative refractive index when accompanied by one or more other dopants which are not downdopants.

Likewise, one or more other dopants which are not downdopants may be present in a region of an optical fiber having a negative relative refractive index.

The term "a-profile" or "alpha profile" refers to a relative refractive index profile, expressed in terms of $\Delta(r)$ which is in units of "%", where r is radius, which follows the equation, $$\Delta(r)=\Delta(r_o)(1-[r-r_0|/(r_1-r_o)]^\alpha),$$

where $r_o$ is the point at which $\Delta(r)$ is maximum, $r_1$ is the point at which $\Delta(r)$ % is zero, and r is in the range $r_1 \leq r \leq r_f$, where $\Delta$ is defined above, $r_1$ is the initial point of the a-profile, $r_f$ is the is final point of the a-profile, and $\alpha$ is an exponent which is a real number.

As used herein, the term "parabolic" therefore includes substantially parabolically shaped refractive index profiles which may vary slightly from an $\alpha$ value of 2.0 at one or more points in the core, as well as profiles with minor variations and/or a centerline dip. In some exemplary embodiments, a is greater than 1.5 and less than 2.5, more preferably greater than 1.7 and less than 2.3 and even more preferably between 1.8 and 2.3 as measured at 850 nm. In other embodiments, one or more segments of the refractive index profile have a substantially step index shape with an $\alpha$ value greater than 8, more preferably greater than 10 even more preferably greater than 20 as measured at 850 nm.

The term "nano-structured fiber region" describes a fiber having a region or area with a large number of gas filled voids, or other nano-sized structures. The region or area may have, for example, more than 50 voids, or more than 100 voids, or even more than 200 voids in the cross-section of the fiber. The gas filled voids may contain, for example, $SO_2$, Kr, Ar, $CO_2$, $N_2$, $O_2$, or mixture thereof. The cross-sectional size (e.g., diameter) of nano-sized structures (e.g., voids) as described herein may vary from about 10 nm to about 1.0 μm (for example, from about 50 nm to about 500 nm), and the length may vary from about 1.0 millimeter to about 50 meters (for example, from about 2.0 mm to about 5.0 meters, or from about 5.0 mm to about 1.0 meters).

In standard single mode or multimode optical fibers, the losses at wavelengths less than 1300 nm are dominated by Rayleigh scattering. These Rayleigh scattering losses $L_s$ are determined by the properties of the material and are typically about 20 dB/km for visible wavelengths (400-700 nm). Rayleigh scattering losses also have a strong wavelength dependence (i.e., $L_S \propto 1/\lambda^4$, see FIG. 4B, comparative fiber A), which means that at least about 1.0 km to about 2.0 km of the fiber is needed to dissipate more than 95% of the input light. Shorter lengths of such fiber would result in lower illumination efficiency, while using long lengths (about 1.0 km to about 2.0 km, or more) can be more costly and can be difficult to manage.

In certain configurations of lighting applications it is desirable to use shorter lengths of fiber, for example, having a length of about 0.02 meters to about 100 meters. This requires an increase of scattering loss from the fiber, while being able to maintain good angular scattering properties (uniform dissipation of light away from the axis of the fiber) and good bending performance to avoid bright spots at fiber bends. A desirable attribute of at least some of the embodiments described herein is uniform and high illumination along the length of the fiber illuminator. Because the optical fiber is flexible, it allows a wide variety of the illumination shapes to be deployed. It is preferable to have no bright spots (due to elevated bend losses) at the bending points of the fiber, such that the illumination provided by the fiber does not vary by more than about 30%, preferably by less than about 20% and more preferably by less than about 10%. For example, in at least some embodiments, the average scattering loss of the fiber is greater than about 50 dB/km, and the scattering loss does not vary more than about 30% (i.e., the scattering loss is within ±30% of the average scattering loss) over any given fiber segment having a length of about 0.2 meters. The average scattering loss of the fiber may be greater than about 50 dB/km with the scattering loss varying by less than about 30% over fiber segments of having a length of less than about 0.05 meters. The average scattering loss of the fiber may be greater than about 50 dB/km with the scattering loss varying by less than about 30% over fiber segments having a length of about 0.01 meters. The average scattering loss of the fiber may also be greater than about 50 dB/km with the scattering loss varying by less than about 20%, and preferably by less than about 10% over fiber segments having a length of about 0.01 meters.

According to embodiments of the present disclosure, the intensity variation of the integrated light intensity diffused through sides of the fiber at the illumination wavelength is less than about 30% for the target length of the fiber, which can be, for example, between about 0.02 meters to about 100 meters. The integrated light intensity diffused through sides of the fiber at a specified illumination wavelength can be varied by incorporating fluorescent material in the cladding or coating. The wavelength of the light scattering by the fluorescent material is different from the wavelength of the light propagating in the fiber.

Fiber designs described herein include a nano-structured fiber region (region with nano-sized structures) placed in the core area of the fiber, or very close to the core. The fiber have scattering losses in excess of about 50 dB/km, for example, greater than about 100 dB/km, greater than about 200 dB/km, greater than about 500 dB/km, greater than about 1000 dB/km, greater than about 3000 dB/km, or even greater than about 5000 dB/km. The scattering loss, and thus illumination, or light radiated by the fiber, is uniform in angular space.

In order to reduce or to eliminate bright spots as bends in the fiber, it is desirable that the increase in attenuation at a 90° bend in the fiber is less than about 5.0 dB/turn, for example, less than about 3.0 dB/turn, less than about 2.0 dB/turn, or even less than about 1.0 dB/turn when the bend diameter is less than about 50 mm. In exemplary embodiments, these low bend losses are achieved at even smaller bend diameters, for example, less than about 20 mm, less than about 10 mm, or even less than about 5.0 mm. The total increase in attenuation may be less than about 1.0 dB per 90 degree turn at a bend radius of about 5.0 mm.

The bending loss is equal to or is less than the intrinsic scattering loss from the core of the straight fiber. The intrinsic scattering is predominantly due to scattering from the nano-sized structures. Thus, according to at least the bend insensitive embodiments of optical fiber, the bend loss does not exceed the intrinsic scattering of the fiber. However, because scattering level is a function of bending diameter, the bending deployment of the fiber depends on its scattering level. For example, the fiber may have a bend loss of less than about 3.0 dB/turn, or even less than about 2.0 dB/turn, and the fiber can be bent in an arc with a radius as small as about 5.0 mm without forming bright spots.

According to some embodiments, the light diffusing fiber 12 includes a core at least partially filled with nanostructures for scattering light, a cladding surrounding the core, and may optionally include at least one coating surrounding the cladding. For example, the core and cladding may be surrounded by primary and secondary coating layers, and/or by an ink layer. In some embodiments, the ink layer contains pigments to provide additional absorption and modify the spectrum of the light scattered by the fiber (e.g., to provide additional color(s) to the diffused light). In other embodiments, one or more of the coating layers comprises molecules which convert the wavelength of the light propagating through the fiber core such that the light emanating from the fiber coating (light diffused by the fiber) is at a different wavelength. In some embodiments, the ink layer and/or the coating layer may comprise phosphor in order to convert the scattered light from the core into light of differing wavelength(s). In some embodiments, the phosphor and/or pigments are dispersed in the primary coating. In some embodiments the pigments are dispersed in the secondary coating, in some embodiments the pigments are dispersed in the primary and secondary coatings. In some embodiments, the phosphor and/or pigments are dispersed in the polymeric cladding. Preferably, the nanostructures are $SO_2$ filled voids.

According to some embodiments, the optical fiber 12 includes a primary coating, an optional secondary coating surrounding the primary coating and/or an ink layer (for example located directly on the cladding, or on one of the coatings. The primary and/or the secondary coating may include at least one of: pigment, phosphors, fluorescent material, hydrophilic material, light modifying material, or a combination thereof.

According to some embodiments, a light diffusing optical fiber includes: (1) a glass core, a cladding, and a plurality of nano-sized structures situated within said core or at a core-cladding boundary, the optical fiber further including an outer surface and is configured to (i) scatter guided light via said nano-sized structures away from the core and through the outer surface, (ii) have a scattering-induced attenuation greater than 50 dB/km at illumination wavelength; and (2) one or more coatings, such that either the cladding or at least one coating includes phosphor or pigments. According to some embodiments, these pigments may be capable of altering the wavelength of the light such that the illumination (diffused light) provided by the outer surface of the fiber is of a different wavelength from that of the light propagating through fiber core. Preferably, the nanostructures are $SO_2$ filled with voids.

According to some embodiments, a light diffusing optical fiber includes: a glass core, a cladding, and a plurality of nano-sized structures situated within said core or at a core-cladding boundary. The optical fiber further includes an outer surface and is configured to (i) scatter guided light via said nano-sized structures away from the core and through the outer surface, (ii) have a scattering-induced attenuation greater than 50 dB/km at illumination wavelength; wherein the entire core includes nano-sized structures. Such fiber may optionally include at least one coating, such that either the cladding or at least one coating includes phosphor or pigments. According to some embodiments the nanostructures are $SO_2$ filled voids.

According to some embodiments, a light diffusing optical fiber includes: a glass core, and a plurality of nano-sized structures situated within said core such that the entire core includes nano-structures, the optical fiber further including an outer surface and is configured to (i) scatter guided light via said nano-sized structures away from the core and through the outer surface, (ii) have a scattering-induced attenuation greater than 50 dB/km at illumination wavelength, wherein the fiber does not include cladding. According to some embodiments, the nanostructures are $SO_2$ filled voids. The $SO_2$ filled voids in the nano-structured area greatly contribute to scattering (improve scattering).

According to some embodiments, a light diffusing optical fiber includes: a glass core, and a plurality of nano-sized structures situated within said core such that the entire core includes nano-structures, said optical fiber further including an outer surface and is configured to (i) scatter guided light via said nano-sized structures away from the core and through the outer surface, (ii) have a scattering-induced attenuation greater than 50 dB/km at illumination wavelength wherein said fiber does not include cladding. According to some embodiments, the fiber optionally includes at least one coating such that either the cladding or the coating includes phosphor or pigments. According to some embodiments, the nanostructures are $SO_2$ filled voids. As stated above, the $SO_2$ filled voids in the nano-structured area greatly contribute to scattering (improve scattering).

Figure 2:
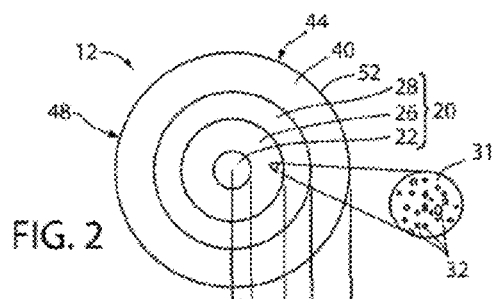
FIG. 2 is a schematic cross-section of the optical fiber of FIG. 1 as viewed along the direction 2-2.

FIG. 1 is a schematic side view of a section of a light diffusing fiber with a plurality of voids in the core of the light diffusing optical fiber 12 having a central axis, or centerline 16. FIG. 2 is a schematic cross-section of light diffusing optical fiber 12 as viewed along the direction 2-2 in FIG. 1. Light diffusing optical fiber 12 can be, for example, any one of the various types of optical fiber with a nano-structured fiber region having periodic or non-periodic nano-sized structures 32. As an example, fiber 12 includes a core 20 divided into three sections or regions. The sections or regions include a solid central region 22, a nano-structured ring portion 26, and an outer, solid portion 28 surrounding the nano-structured ring portion 26. A cladding 40 surrounds the core 20 and has an outer surface. The cladding 40 can be, for example, a low index polymer such as UV or thermally curable fluoroacrylate or silicone. The cladding 40 may include pure low index polymer. Additionally, the cladding 40 may also include pure or F-doped silica. The cladding 40 may have low refractive index to provide a high numerical aperture (NA). The NA of fiber 12 may be equal to, or greater than, the NA of a light source directing light into the fiber 12. According to embodiments of the present disclosure, the NA of fiber 12 may be greater than about 0.2, greater than about 0.3, or even greater than about 0.4.

According to exemplary embodiments, the nano-structured ring portion 26 of light diffusing fiber 12 comprises a glass matrix 31 with a plurality of non-periodically disposed nano-sized structures 32 situated therein, such as the example voids shown in detail in the magnified inset of FIG. 2. The voids may be periodically disposed, such as in a photonic crystal optical fiber, wherein the voids typically have diameters between about $1.0 \times 10^{-6}$ m and about $1.0 \times 10^{-5}$ m. The diameters of the voids may be at least about 10 nm. The voids may also be non-periodically or randomly disposed. The glass matrix 31 in nano-structured ring portion 26 may be for example, but without limitation, a fluorine-doped silica or an undoped pure silica.

The nano-sized structures 32 scatter the light away from the core 20 and toward the outer surface of the fiber. The scattered light is then diffused through the outer surface of the fiber 12 to provide illumination. That is, most of the light is diffused via scattering through the sides of the fiber 12 along the fiber length. According to embodiments of the present disclosure, the fiber emits substantially uniform radiation over its length, and the fiber has a scattering-induced attenuation of greater than about 50 dB/km in the illumination wavelength. The scattering-induced attenuation may be greater than about 100 dB/km, greater than about 500 dB/km, greater than about 1000 dB/km, greater than about 2000 dB/km, or even greater than about 5000 dB/km in the illumination wavelength. Such scattering losses are about 2.5 to about 250 times greater than the Rayleigh scattering losses in standard single mode and multimode optical fibers. The amount of the loss via scattering can be increased by changing the properties of the fiber 12, the width of the nano-structured region 26, and the size and the density of the nano-sized structures 32.

In some embodiments, nano-structured region 26 includes pure silica including a plurality of nano-sized structures 32. The minimum relative refractive index and the average effective relative refractive index of nano-structured region 26, taking into account the presence of any voids, may both be less than about −0.1%. The nano-sized structures 32, or voids, may contain one or more gases, such as argon, nitrogen, oxygen, krypton, or $SO_2$ or can contain a vacuum with substantially no gas. However, regardless of the presence or absence of any gas, the average refractive index in nano-structured region 26 is lowered due to the presence of nano-sized structures 32. Nano-sized structures 32 can be randomly or non-periodically disposed in the nano-structured region 26. Alternatively, nano-sized structures 32 may be disposed periodically in the nano-structured region 26.

According to exemplary embodiments, solid central region 22 may include germania doped silica, core inner annular region 28 may include pure silica, and the cladding 40 may include a glass or a low index polymer. The nano-structured region 26 may include a plurality of nano-sized structures 32 in pure silica, or, alternatively, nano-structured region 26 may include a plurality of nano-sized structures 32 in fluorine-doped silica. According to other exemplary embodiments, the entire core 20 may be nano-structured (filled with voids, for example), with the core 20 being surrounded by the cladding 40. The core 20 may have a "step" refractive index delta, or may have a graded core profile, with a-profile having, for example, α-value between about 1.8 and about 2.3.

Glass in solid central region 22 and core inner annular region 28 may include updopants, such as Ge, Al, Ti, P and combinations thereof. By "non-periodically disposed" or "non-periodic distribution," it is meant that when one takes a cross-section of the optical fiber, such as shown in FIG. 2, the nano-sized structures 32 are randomly or non-periodically distributed across a portion of the fiber. As an example, where the nano-sized structures 32 include voids, similar cross-sections taken at different points along the length of the fiber will reveal different cross-sectional void patterns, i.e., various cross-sections will have different voids patterns, wherein the distributions of voids and sizes of voids do not match. That is, the voids are non-periodic, i.e., they are not periodically disposed within the fiber structure. These voids are stretched (elongated) along the length (i.e. parallel to the longitudinal axis) of the optical fiber, but do not extend the entire length of the entire fiber for typical lengths of transmission fiber. The voids may extend less than about 10 meters, and in many cases less than about 1.0 meter along the length of the fiber 12.

As described above, solid central region 22 and core inner annular region 28 may include silica doped with germanium, i.e., germania-doped silica. Dopants other than germanium, singly or in combination, may be employed within the core, and particularly at or near the centerline 16, of the optical fiber 12 to obtain the desired refractive index and density. The relative refractive index profile of the optical fiber 12 disclosed herein is non-negative in core sections solid central region 22 and core inner annular region 28. The optical fiber may contain no index-decreasing dopants in the core. Additionally, the relative refractive index profile of the optical fiber 12 may be non-negative in solid central region 22, nano-structured ring portion 26 and/or core inner annular region 28.

The fiber 12 optionally includes a coating 44 surrounding the cladding 40. Coating 44 may include a low modulus primary coating layer and a high modulus secondary coating layer. The coating 44 may be a polymer coating such as an acrylate-based or silicone based polymer. The coating may have a constant diameter along the length of the fiber. The coating 44 may be designed to enhance the distribution and/or the nature of light that passes from core 20 through cladding 40. The outer surface of the cladding 40 or the outer surface or the optional coating 44 represents the sides 48 of fiber 12 through which light traveling in the fiber exits via scattering, as described herein. The coating 44 may be a resin that transmits UV light. For example, the resin that transmits UV light may be, but is not limited to, resins having structutes of: tripropylene glycol diacrylate (TPGDA), polyester tetraacrylate, polyester hexaacrylate, aliphatic urethane diacrylate+hexanediol diacrylate, polyether tetraacrylate, silicone diacrylate, silicone hexaacrylate, epoxydiacrylate based on bisphenol A, and epoxydiacrylate based on bisphenol A+25% TPGDA.

According to embodiments of the present disclosure, core 20 may be a graded-index core, and may have a refractive index profile having a parabolic (or substantially parabolic) shape. For example, the refractive index profile of core 20 may have an α-shape with an α value of about 2.0 as measured at 850 nm. The a value may be between about 1.8 and about 2.3. According to other exemplary embodiments, one or more segments of the refractive index profile may have a substantially step index shape with an α value greater than about 8.0, or greater than about 10, or even greater than about 20, as measured at 850 nm. The refractive index of the core may have a centerline dip, wherein the maximum refractive index of the core 20, and the maximum refractive index of the entire optical fiber 12, is located a small distance away from centerline 16. Alternatively, the refractive index of the core 20 has no centerline dip, and the maximum refractive index of the core 20, and the maximum refractive index of the entire optical fiber 12, is located at the centerline. According to exemplary embodiments, the refractive index of fiber 12 may have radial symmetry.

According to embodiments of the present disclosure, fiber 12 has a silica-based core 20 and depressed index (relative to silica) polymer cladding 40. The low index polymer cladding 40 may have a relative refractive index that is negative. For example, the relative refractive index of the low index polymer cladding 40 may be less than about −0.5%, or even less than about −1.0%. The cladding 40 may have a thickness of greater than about 20 μm, and the outer diameter of the cladding 40 may have a constant diameter along the length of fiber 12. The cladding 40 may have a lower refractive index than the core 20, and a thickness of greater than about 10 μm. The cladding 40 may have an outer diameter of $2 \times R_{max}$. For example, the cladding 40 may have an outer diameter of about 125 μm, such as between about 120 μm and 130 μm, or between about 123 μm and about 128 μm. Alternatively, the cladding 40 may have a diameter that is less than about 120 μm, such as between about 60 μm and about 80 μm.

The outer diameter $R_c$ of core 20 may be constant along the length of the fiber 12. Additionally, the outer diameters of solid central region 22, nano-structured ring portion 26 and core inner annular region 28 may also be constant along the length of the fiber 12. By constant, it is meant that the variations in the diameter with respect to the mean value are, for example, less than about 10%, or less than about 5.0%, or even less than about 2.0%.

Figure 3A:
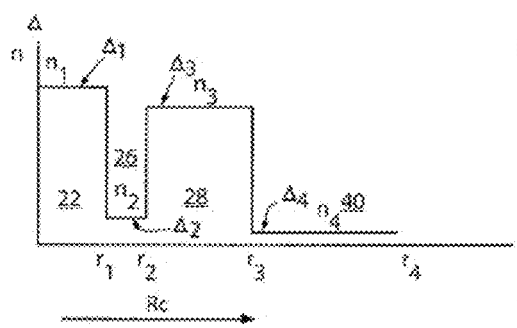
FIG. 3A is a schematic illustration of relative refractive index plot versus fiber radius for an exemplary embodiment of light diffusing fiber.

The outer radius $R_c$ of core 20 may be greater than about 10 μm and less than about 600 μm, for example, between about 30 μm and about 400 μm, or between about 125 μm and about 300 μm. The outer radius $R_c$ of core 20 may be between about 50 μm and about 250 μm. As shown in FIG. 3A, the outer radius $R_c$ of core 20 is equal to the outer radius $R_3$ of core inner annular region 28.

The solid central region 22 may have a radius $R_1$ such that $0.1R_c \leq R_1 \leq 0.9R_c$, or such that $0.5R_c \leq R_1 \leq 0.9R_c$. $R_1$ may be between about 24 μm and about 50 μm such that the diameter of the solid central region 22 is between about 48 μm and 100 μm. For example, $R_1$ may be greater than about 24 μm, greater than about 30 μm, or even greater than about 40 μm. The nano-structured ring region 26 may have a width $W_2$ such that $0.05R_c \leq W_2 \leq 0.9R_c$, or such that $0.1R_c \leq W_2 \leq 0.9R_c$. Additionally, width $W_2$ may be $0.5R_c \leq W_2 \leq 0.9R_c$. According to embodiments of the present disclosure, a wider nano-structured region 26 provides a higher scattering-induced attenuation for the same density of nano-sized structures 32. The radial width $W_2$ of nano-structured region 26 may be greater than about 1.0 μm. For example, $W_2$ may be between about 5.0 μm and about 300 μm, such as less than about 200 μm. $W_2$ may also be, for example, between about 2.0 μm and about 100 μm, between about 2.0 μm and about 50 μm, between at least 2.0 μm and about 20 μm, or even between about 2.0 μm and about 12 μm. $W_2$ may be, for example, at least about 7.0 μm. The core inner annular region 28 may have a width $W_3$ such that $W_3 = R_3 - R_2$ and has a midpoint $R_{3MID} = (R_2 + R_3)/2$. The core inner annular region 28 may have a width $W_3$ such that $0.1R_c > W_3 > 0.9R_c$. For example, $W_3$ may be between about 1.0 μm and about 100 μm. Additionally, the cladding 40 has a radius $R_4$, which is also the outermost periphery of the optical fiber 12. The width of the cladding 40, which is equal to $R_4 - R_3$, may be, for example, greater than about 20 μm, or greater than about 50 μm, or even greater than about 70 μm.

FIG. 3A is a plot of the exemplary relative refractive index Δ versus fiber radius for an example fiber 12 shown in FIG. 2 (solid line). The core 20 may also have a graded core profile, with a-profile having, for example, α-value between about 1.7 and about 2.3 (e.g., about 1.8 to about 2.3). Solid central region 22 extends radially outwardly from the centerline to its outer radius, $R_1$, and has a relative refractive index profile $\Delta_1(r)$ corresponding to a maximum refractive index $n_1$ (and relative refractive index percent $\Delta_{1MAX}$). According to the embodiment of FIG. 3A, the reference index $n_{REF}$ is the refractive index at the cladding. The nano-structured region 26 has minimum refractive index $n_2$, a relative refractive index profile $\Delta_2(r)$, a maximum relative refractive index $\Delta_{2MAX}$, and a minimum relative refractive index $\Delta_{2MIN}$, wherein some embodiments $\Delta_{2MAX} = \Delta_{2MIN}$. The core inner annular region 28 has a maximum refractive index $n_3$, a relative refractive index profile $\Delta_3(r)$ with a maximum relative refractive index $\Delta_{3MAX}$ and a minimum relative refractive index $\Delta_{3MIN}$, wherein some embodiments $\Delta_{3MAX} = \Delta_{3MIN}$. As further shown in FIG. 3A, the cladding 40 has a refractive index $n_4$, a relative refractive index profile $\Delta_4(r)$ with a maximum relative refractive index $\Delta_{4MAX}$ and a minimum relative refractive index $\Delta_{4MIN}$. In some embodiments, $\Delta_{4MAX} = \Delta_{4MIN}$. In some embodiments, $\Delta_{1MAX} > \Delta_{4MAX}$ and $\Delta_{3MAX} > \Delta_{4MAX}$. In some embodiments $\Delta_{2MIN} > \Delta_{4MAX}$. In the embodiment shown in FIGS. 2 and 3A, $\Delta_{1MAX} > \Delta_{3MAX} > \Delta_{2MAX} > \Delta_{4MAX}$, and the refractive indices of the regions have the following relationship $n_1 > n_3 > n_2 > n_4$.

Solid central region 22 and core inner annular region 28 may have a substantially constant refractive index profile, as shown in FIG. 3A with a constant $\Delta_1(r)$ and $\Delta_3(r)$. In addition, $\Delta_2(r)$ may be either slightly positive ($0 < \Delta_2(r) < 0.1\%$), negative ($-0.1\% < \Delta_2(r) < 0$), or substantially constant. The absolute magnitude of $\Delta_2(r)$ may be less than about 0.1%, for example, less than about 0.05%. According to embodiments of the present disclosure, absolute magnitude of $\Delta_2(r)$ may be less than about 0.025%, or even less than about 0.01%, for more than about 50% of the radial width of the nano-structured ring portion 26. The cladding 40 may have a substantially constant refractive index profile, as shown in FIG. 3A with a constant $\Delta_4(r)$, where $\Delta 4(r) = 0\%$. In some embodiments the cladding 40 may have a refractive index $-0.05\% < \Delta_4(r) < 0.05\%$. The solid central region 22 may have a refractive index where $\Delta_1(r) > 0\%$. Additionally, nano-structured ring portion 26 may have a relative refractive index profile $\Delta_2(r)$ having a negative refractive index with absolute magnitude less than about 0.05%, and $\Delta_3(r)$ of core inner annular region 28 may be, for example, positive or zero. In at least some embodiments, $n_1 > n_2$ and $n_3 > n_4$.

Figure 3B:
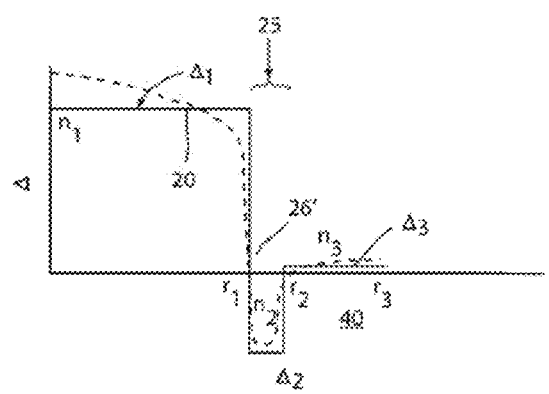
FIG. 3B is a schematic illustration of relative refractive index plot versus fiber radius for another exemplary embodiment of light diffusing fiber.

FIG. 3B schematically illustrates an exemplary embodiment of light diffusing fiber 12. As shown, the fiber 12 includes a core 20 with a relative refractive index $\Delta_1$ and a nano-structured region 26' situated over and surrounding the core 20. The core 20 may have a step index profile, or a graded core profile, with a-profile having, for example, α-value between about 1.8 and about 2.3. The nano-structured region 26' is an annular ring with a plurality of voids. The width of nano-structured region 26' may be as small as about 1.0 μm to about 2.0 μm, and may have a negative average relative refractive index $\Delta_2$. The cladding 40 surrounds the nano-structured region 26', the cladding 40 having a width that may be as small as about 1.0 μm. The cladding 40 may have a negative, a positive or a substantially constant relative refractive index. The main difference between the examples shown in FIGS. 3A and 3B is that nano-structured region 26 shown in FIG. 3A is located in the core 20 of the light diffusing fiber 12, and nano-structured region 26' shown in FIG. 3B is located at the interface of the core 20 and the cladding 40. In the direction moving radially outwardly from the centerline, the nano-structured region 26' begins where the relative refractive index of the core first reaches a value of less than about $-0.05\%$. In the embodiment shown in FIG. 3B, the cladding 40 has a relative refractive index profile $\Delta_3(r)$ having a maximum absolute magnitude less than about 0.1%, where $\Delta_{3MAX} < 0.05\%$ and $\Delta_{3MIN} > -0.05\%$, and the nano-structured region 26' ends where the outmost void occurs in the void-filled region. Additionally, as shown in FIG. 3B, the index of refraction of the core 20 is greater than the index of refraction $n_2$ of the nano-structured region 26', and the index of refraction $n_1$ of the cladding 40 is also greater than the index of refraction $n_2$ of nano-structured region.

Figure 3C:
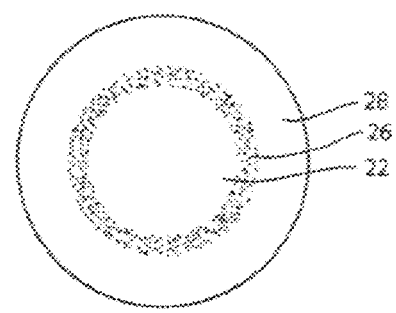
FIG. 3C illustrates another exemplary embodiment of a light diffusing fiber.

FIG. 3C illustrates an embodiment of an optical fiber 12 in accordance with the present disclosure. The fiber 12, which was made, has a core region 22, a nano-structured region 26, a third core region 26 and a polymer cladding 40. The fiber 12 had a first core region 22 with an outer radius $R_1$ of about 33.4 μm, a nano-structured region 26 with an outer radius $R_2$ of about 42.8 µm, a third core region 28 with an outer radius $R_3$ of about 62.5 µm, and a polymer cladding 40 (not shown) with an outer radius $R_4$ of about 82.5 µm. The material of the core was pure silica, the material of the cladding 40 was a low index polymer (e.g., UV curable silicone having a refractive index of 1.413 commercially available from Dow-Corning of Midland, Mich. under product name Q3-6696). The fiber 12 had an NA of 0.3. The fiber 12 included nano-sized structures containing $SO_2$ gas. Applicants found that filled $SO_2$ voids in the nano-structured ring 26 greatly contribute to scattering. Furthermore, when $SO_2$ gas was used to form the nano-structures, it has been discovered that this gas allows a thermally reversible loss to be obtained, i.e., below 600° C. the nano-structured fiber scatters light, but above 600° C. the same fiber will guide light. This unique behavior that $SO_2$ imparts is also reversible, in that upon cooling the same fiber below 600° C., the fiber 12 will act as light diffusing fiber and will again generate an observable scattering effect.

The light diffusing fiber 12 according to embodiments of the present disclosure can be made by methods which utilize preform consolidation conditions which result in a significant amount of gases being trapped in the consolidated glass blank, thereby causing the formation of voids in the consolidated glass optical fiber preform. Rather than taking steps to remove these voids, the resultant preform is used to form an optical fiber with voids, or nano-sized structures, therein. The resultant fiber's nano-sized structures or voids are utilized to scatter or guide the light out of the fiber, via its sides, along the fiber length. That is, the light is guided away from the core 20, through the outer surface of the fiber, to provide desired illumination.

As used herein, the diameter of a nano-sized structure such as a void is the longest line segment contained within the nano-sized structure whose endpoints are at the boundary of the nano-sized structure when the optical fiber is viewed in perpendicular cross-section transverse to the longitudinal axis of the fiber. A method of making optical fibers with nano-sized voids is described, for example, in U.S. Patent Application Publication No. 2007/0104437 A1, which is incorporated herein by reference.

According to embodiments of the present disclosure, light diffusing fiber 12 provides uniform illumination along the length of the fiber 12. The light scattering axially from the surface of the fiber has a variation relative to the mean scattering intensity that is less than about 50%, less than about 30%, less than about 20%, or even less than about 10%. The dominant scattering mechanism in conventional silica-based optical fibers without nano-sized structures is Rayleigh scattering, which has a broad angular distribution. The uniformity of illumination along the fiber length may be controlled such that the minimum scattering illumination intensity is not less than about 0.7 of the maximum scattering illumination intensity. As described below, such minimum scattering illumination intensity may be achieved by controlling fiber tension during the draw process, or by selecting the appropriate draw tension. Appropriate draw tensions may be, for example, between about 30 g and about 100 g, or between about 40 g and about 90 g.

Figure 4A:
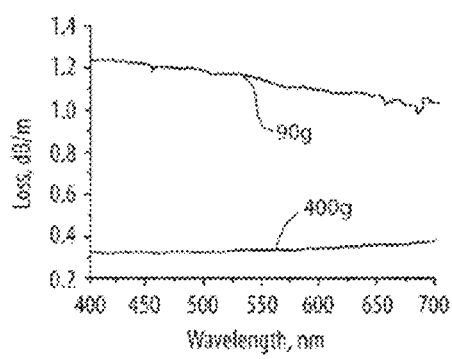
FIGS. 4A and 4B depict fiber attenuation (loss) in dB/m versus wavelength (nm)
Figure 4B:
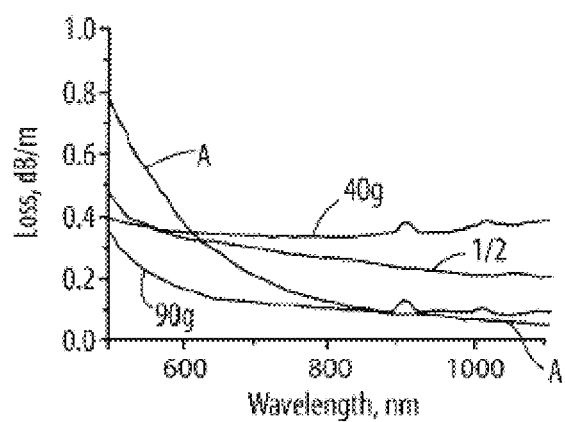

FIG. 4A is a plot of attenuation versus wavelength for a fiber such as shown in FIG. 3C which included $SO_2$ gas filled voids. The figure depicts attenuation as a function of wavelength for a light diffusing fiber 12 drawn at a tension of 90 g and a light diffusing fiber 12 drawn at a tension of 400 g. FIG. 4A illustrates that light diffusing fibers 12 can achieve very large scattering losses, and thus can provide high illumination intensity, in the visible wavelength range. More specifically, FIG. 4A illustrates that higher fiber draw tensions result in lower scattering losses and that lower fiber draw tensions result in a fiber section with higher scattering loss, and thus, stronger illumination.

FIG. 4B is a plot of attenuation versus wavelength for a light diffusing fiber 12 drawn at a tension of 90 g, a light diffusing fiber 12 drawn at a tension of 40 g, a comparative multiple mode fiber (labeled fiber A) with normalized loss, and a theoretical fiber having a loss dependence of $1/\lambda$. The light diffusing fibers 12 shown in FIG. 4B included nano-sized structures containing $SO_2$ gas. (The graph of FIG. 4B depicts wavelength dependence of the loss. In this example, in order to compare the slope of the scattering for the light fiber 12 and fiber A, the loss of low loss fiber (fiber A) was multiplied by a factor of 20, so that the two plots can be easily shown in the same Figure). As shown, the average spectral attenuation from 400 nm to 1100 nm was about 0.4 dB/m for the fiber drawn with a tension of about 40 g, and was about 0.1 dB/m for the fiber drawn with a tension of about 90 g. FIG. 4B illustrates that optical fiber 12 has a relatively flat (weak) dependence on wavelength as compared to standard single-mode transmission fiber, such as for example, SMF-28e$^R$ fiber. In standard single mode or multimode optical fibers, the losses at wavelengths less than about 1300 nm are dominated by Rayleigh scattering. These Rayleigh scattering losses are determined by the properties of the material and are typically about 20 dB/km for visible wavelengths between about 400 nm and about 700 nm where Rayleigh scattering losses are proportional to $\lambda^{-p}$, where p is about 4. In contrast, light diffusing fiber 12 according to the present disclosure, have scattering losses proportional to $1/\lambda^{-p}$, where p is less than 2, less than 1, or even more less than 0.5. According to embodiments of the present disclosure, p may be less than 2, less than 1, or even more less than 0.5 over at least about 80% of the wavelength range of 400 nm-1100 nm.

Without being bound to any particular theory, it is believed that the increase in the scattering losses when the draw tension decreases, for example from about 90 g to about 40 g, is due to an increase in the average diameter of the nanostructures. Therefore, this effect of fiber tension could be used to produce constant attenuation along the length of the fiber by varying the fiber tension during the draw process. For example, a first fiber segment drawn at high tension, $T_1$, with a loss of $\alpha_1$ and length, $L_1$, will attenuate the optical power from an input level P0 to P0 exp($-\alpha_1*L_1/4.343$). A second fiber segment optically coupled to the first fiber segment and drawn at lower tension $T_2$ with a loss of $\alpha_2$ and length $L_2$ will further attenuate the optical power from P0 exp($-\alpha_1*L_1/4.343$) to P0 exp($-\alpha_1*_L1/40.343$) exp($-\alpha_2*L_2/4.343$). The lengths and attenuations of the first and second fiber segments can be adjusted to provide uniform intensity along the length of the concatenated fiber.

Embodiments of the present disclosure further relate to medical devices having interior channels, and to systems for disinfecting medical devices having interior channels. For ease of discussion, a flexible endoscope is used to illustrate such medical devices. However, it should be understood that embodiments of the present disclosure may include any medical device having at least one interior channel, and particularly to medical devices which are conventionally used to perform more than one procedure such that it is recommended that they be disinfected between uses. For example, such medical devices may also be, but are not limited to, laparoscopic devices, indwelling catheters, nonindwelling catheters, IV and other medical tubing (i.e. feeding or ventilation tubes), luminal surgical equipment, dental devices, arthroscopic shavers, and inflow/outflow cannulas. Additionally, it should be understood that an interior channel is not limited to those of the illustrated flexible endoscope. As used herein, an interior channel may be, but is not limited to, any passage fluidly connecting one opening of a medical device to another opening of a medical device.

Figure 5:
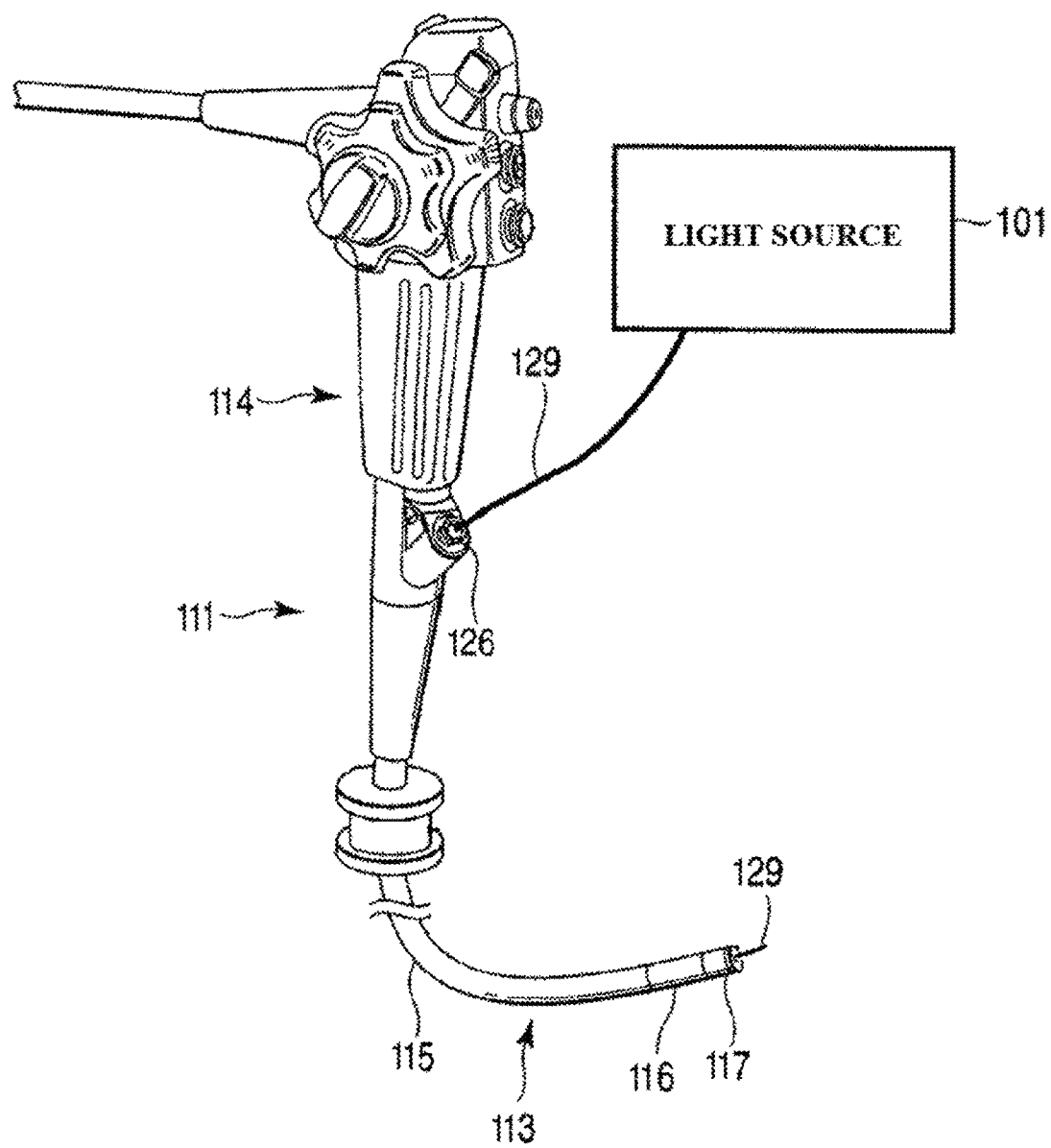
FIG. 5 is a schematic illustration of an endoscopic surgical system according to an embodiment of the present disclosure.

FIG. 5 is a schematic illustration of an endoscopic surgical system according to an embodiment of the present disclosure. The endoscopic surgical system includes an endoscope 111 and an operation section 114. The endoscope 111 includes an elongated insertion portion 113 having a proximal end portion configured to be coupled to the operation section 114. The insertion portion 113 is configured to be inserted into the body of a patient. The insertion portion 113 includes an elongated flexible tube portion 115, a bending portion 116 coupled to a distal end of the flexible tube portion 115, and a distal end hard portion 117 coupled to a distal end of the bending portion 116. The operation section 114 includes features, such as knobs, that control the bending portion 116 to bend in different directions, such as, but not limited to, upward, downward, leftward and rightward directions. The operation section 114 also includes channel port 126 which communicates with a use channel 150 (shown in FIG. 7) for the insertion of surgical instruments.

Figure 6:
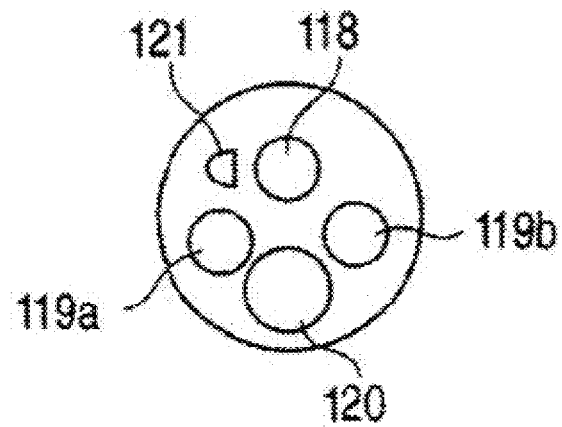
FIG. 6 is a front view of a distal end face of an endoscope according to an embodiment of the present disclosure.

FIG. 6 is a front view of a face of the distal end hard portion of an endoscope in accordance with embodiments of the present disclosure. The distal end hard portion 117 includes an observation window 118, illumination windows 119a and 119b, a use opening 120, and a gas-feeding/water-feeding nozzle 121. The configuration of the distal end hard portion 117 shown in FIG. 6 is merely exemplary and is not intended to limit embodiments of the present disclosure to any particular configuration. It should be understood that the different features may be positioned on the face of the distal end hard portion 117 in any manner. It should further be understood that some embodiments of the present disclosure may not include all the features shown in FIG. 6 and that various different combinations of the observation window 118, the illumination windows 119a and 119b, the use opening 120, and the gas-feeding/water-feeding nozzle 121 are comprehended.

Figure 7:
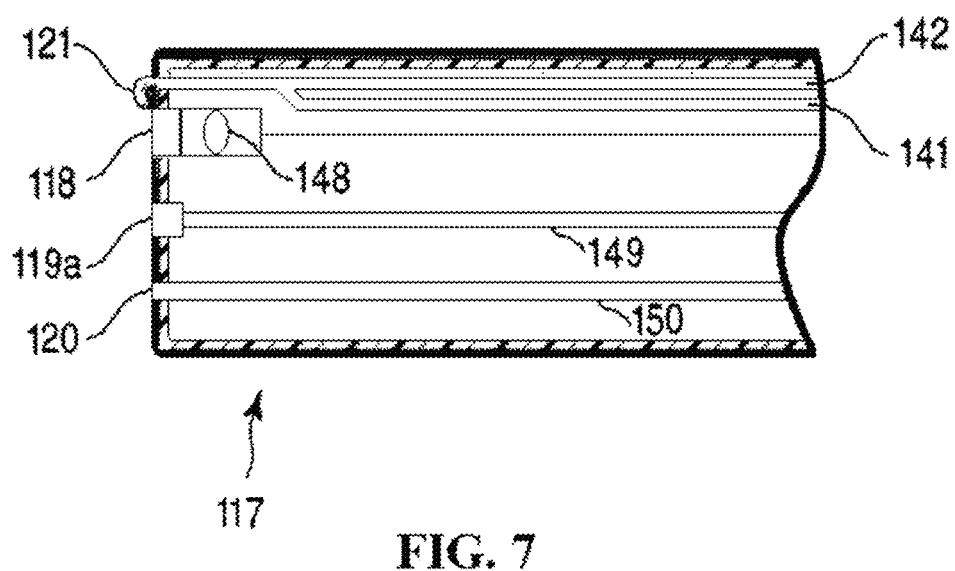
FIG. 7 is a schematic sectional view of a distal end of an endoscope according to an embodiment of the present disclosure.

FIG. 7 is a schematic sectional view of the distal end hard portion of an endoscope according to an embodiment of the present disclosure. As shown, the observation window 118 may be fitted with an imaging section provided with an optical system such as an objective lens 148 and an imaging element such as CCD (not shown). The illumination windows 119a and 119b may be fitted with illumination lenses. The endoscopic surgical system further includes light guides 149 having respective fore end portions disposed in confronting relation with the illumination lenses of windows 119a and 119b. The light guides 149 are detachably connectable to a light source and transmit illumination light from the light source to the respective illumination windows 119a and 119b. The light guides 149 may be, for example, fiber optic cables, or bundles of fiber optic cables. As further shown in FIG. 7, the endoscope includes a use channel 150 which provides a passage for insertion of surgical instruments through use opening 120 and into the body of a patient. The use channel 150 communicates with channel port 126 and surgical instruments may be inserted into channel port 126, through use channel 150 and out of use opening 120 during performance of a surgical procedure.

Additionally, the gas-feeding/water-feeding nozzle 121 is fluidly connected to a source of water through water channel 141 and to a source of gas through gas channel 142.

FIG. 5 also illustrates the insertion of cylindrical optical diffuser 129 into an interior channel of the endoscope 111. As shown, the cylindrical optical diffuser 129 is connected to a light source 101 which is capable of emitting electromagnetic radiation that is in the UV and/or the short wavelength visible light range of wavelengths. The cylindrical optical diffuser 129 may be inserted through the channel port 126 and into at least one interior channel of the endoscope 111 where the cylindrical optical diffuser 129 emits UV or short wavelength visible light to disinfect the at least one interior channel. For example, where channel port 126 communicates with the use channel 150 for insertion of surgical instruments as described above, the cylindrical optical diffuser 129 may be inserted through the channel port 126 and into the use channel 150. Light from the light source 101 may then be introduced into the cylindrical optical diffuser 129 such that the fiber emits UV or short wavelength visible light to disinfect the use channel 150. According to embodiments of the present disclosure, the endoscope 111 may further include ports in communication with water channel 141 and gas channel 142, and at least one cylindrical optical diffuser 129 may be inserted through the ports and into water channel 141 and gas channel 142 where UV or short wavelength visible light may be emitted from the cylindrical optical diffuser 129 to disinfect the channels. Alternatively, the endoscopic surgical system may be disassembled in order to provide access to use channel 150, water channel 141 and/or gas channel 142, and at least one cylindrical optical diffuser 129 may be inserted directly into use channel 150, water channel 141 and/or gas channel 142 where UV or short wavelength visible light may be emitted from the cylindrical optical diffuser 129 to disinfect the channels.

Figure 8:
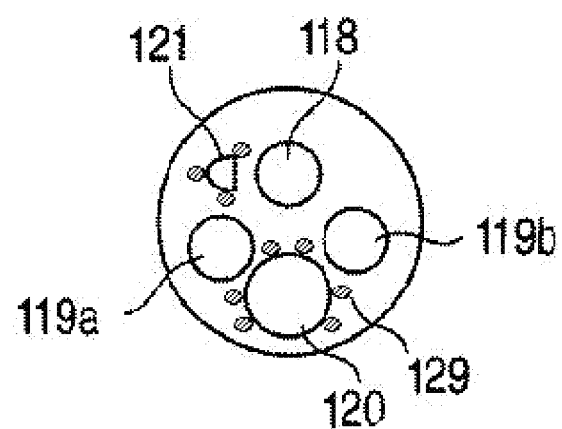
FIG. 8 is a front view of a distal end face of an endoscope according to an embodiment of the present disclosure.

FIG. 8 is a front view of a face of the distal end hard portion of an endoscope in accordance with another embodiment of the present disclosure. The distal end hard portion 117 includes an observation window 118, illumination windows 119a and 119b, a use opening 120, and a gas-feeding/water-feeding nozzle 121. As shown, the endoscope also includes cylindrical optical diffuser 129 physically integrated into the endoscope. The configuration of the integrated cylindrical optical diffusers 129 shown in FIG. 8 is merely exemplary and is not intended to limit embodiments of the present disclosure to any particular configuration. It should also be understood that endoscopes according to the present disclosure could include any number of integrated cylindrical optical diffusers.

FIG. 8 illustrates one exemplary configuration of the cylindrical optical diffusers physically integrated into a medical device. As shown, the endoscope includes cylindrical optical diffusers disposed in optical communication with the use channel 150, the water channel 141 and the gas channel 142. In the embodiment shown in FIG. 8, at least a portion of the wall of the interior channels are formed from a material that is transmissive to UV and/or short wavelength visible light. As such, light for disinfecting the interior channels can be transmitted into the interior channels from the cylindrical optical diffusers which are disposed outside of the channels. According to another embodiment, the cylindrical optical diffusers may be entirely disposed in the interior channels. Alternatively, the cylindrical optical diffusers may be partially disposed in the interior channels such that the volume of the channel which is occupied by the fibers is limited. For example, a portion of the cylindrical optical diffusers may be recessed into the wall of the interior channels. It should be understood that endoscopes according to the present disclosure may include cylindrical optical diffusers integrated into any number of the channels shown in FIG. 8.

Other embodiments of the present disclosure relate to medical devices having interior channels which are positioned in a portion of a patient's body. As explained above, such devices may be, for example, catheters or medical tubing which include an interior channel which has an interior wall, as well as an exterior wall having surfaces which directly contact a portion of the patient. In such embodiments, the interior channel of the medical device is formed from a material that is transmissive to UV and/or short wavelength visible light, and the cylindrical optical diffusers may be disposed on the inside or on the outside of the interior channel. In such embodiments, light for disinfecting the medical device is transmitted to the surfaces of the interior wall, as well as to the surfaces of the exterior wall. The surfaces of the walls of the interior channel of such medical devices can be disinfected while maintaining the position of the device in a portion of the patient's body.

In addition to disinfecting the surfaces of the walls of the interior channel, the light can also be transmitted out of the interior channel to have a disinfecting effect inside the patient's body. For example, the light may disinfect human body substances such as tissue and fluids in the patient's body which may contain bacteria. The insertion of medical devices into the body of a patient has become common practice in many fields of medicine, but is also associated with the risk of bacterial and fungal infections. The mere presence of certain medical devices inside a patient's body may promote growth of bacteria by providing a surface for bacterial adhesion and cause tissue around the medical device to become infected. Similarly, blood, urine, or other fluids within the patient's body, or fluids being transported into or out of the patient's body through the medical device, may also be, or become, infected. One standard response to such infections is to remove the medical device from the patient. However, removing the medical device is not ideal as it defeats the primary purpose of the medical device. Also, due to a variety of circumstances, removing a medical device from some patients is either not possible or not feasible. Alternatively, such infections may be addressed by administering antimicrobial agents. However, the type of bacteria present in the patient must be known in order to select antimicrobial agents to which the bacteria is susceptible. Use of antimicrobial agents to which the bacteria is resistant would fail to have a disinfecting effect and would prolong the infection inside the patient's body. In certain instances, such medical devices may be positioned in a portion of a patient's body for an extended period of time, for example, a period of time longer than about six hours, and disinfecting the medical device may be performed to reduce bacteria that may grow or be present on the surfaces of the medical device. In other instances, such medical devices may be positioned in a portion of a patient's body for the purpose of treating conditions associated with the presence of bacteria inside the patient, such as in the tissue and/or fluids inside of the patient. The cylindrical optical diffusers of such medical devices may be configured to transmit UV and/or short wavelength visible light. However, as it is known that extended exposure to UV light can be harmful to the health of a patient, it may be preferable to instead transmit short wavelength visible light to disinfect the surfaces of the interior channel while the medical device is positioned in a portion of a patient's body. Such short wavelength visible light may be, for example, between about 400 nm and about 450 nm, or between about 405 nm and about 415 nm.

According to embodiments of the present disclosure, the cylindrical optical diffuser may include a coating disposed on an end of the cylindrical optical diffuser opposite an end where light from the light source is input into the cylindrical optical diffuser. The coating may cover at least a portion of the end of the cylindrical optical diffuser such that guided light in the cylindrical optical diffuser is prevented from being transmitted out of the end of the cylindrical optical diffuser. Where the cylindrical optical diffuser is a side-emitting fiber, the coating may cover an end of at least the core and may cover a portion of the surrounding cladding. The coating may be, for example, a reflective coating or an absorptive coating. In certain applications of embodiments of the present disclosure, it may be advantageous to limit the transmission of light from the end of the cylindrical optical diffuser such that substantially all light emitted from the diffuser is emitted through the outer surface of the diffuser.

Embodiments of the present disclosure also relate to disinfection methods. A method according to the present disclosure includes inserting at least a portion of at least one cylindrical optical diffuser into an interior channel of a medical device. For purposes of the present disclosure, inserting at least a portion of at least one cylindrical optical diffuser into an interior channel of a medical device may include any manual or automated process for introducing the cylindrical optical diffuser into the interior channel. Additionally, inserting at least a portion of at least one cylindrical optical diffuser into an interior channel of a medical device may include providing a medical device with an integrated cylindrical optical diffuser, wherein the integrated optical diffuser is configured to emit light into the interior channel. Alternatively, the method may include positioning the cylindrical optical diffuser outside of an interior channel formed from a material that is transmissive to UV and/or short wavelength visible light.

The method further includes introducing light from the light source into the end of the at least one cylindrical optical diffuser optically coupled to the light source and emitting the light through the outer surface of the cylindrical optical diffuser to disinfect at least one surface of the interior channel of the medical device. Light emitted through the outer surface of the cylindrical optical diffuser may also disinfect human body substances such as tissue and fluids in the patient's body which may contain bacteria.

The method of the present disclosure includes exposing the interior channel of the medical device to a dose of light sufficient to disinfect the interior channel of the medical device and/or to disinfect human body substances in the patient's body. The dose of light may be sufficient to reduce greater than 90% of bacteria, fungi, and/or viruses in the interior channel of the medical device. Alternatively, the dose of light may be sufficient to reduce greater than 99% of bacteria, fungi, and/or viruses in the interior channel of the medical device. Where the light is UV light, the dose of light may be, for example, greater than about 5 mJ/cm$^2$, such as between about 5 mJ/cm$^2$ and about 175 mJ/cm$^2$. The dose of light may be between about 10 mJ/cm$^2$ and about 150 mJ/cm$^2$, or even between about 15 mJ/cm$^2$ and about 80 mJ/cm$^2$. Where the light is short wavelength visible light the dose of light may be, for example, greater than about 25 J/cm$^2$, such as between about 25 J/cm$^2$ and about 250 J/cm$^2$. The dose of light may be between about 50 J/cm$^2$ and about 215 J/cm$^2$, or even between about 75 J/cm$^2$ and about 190 J/cm$^2$.

Exposing the interior channel of the medical device to a dose of light sufficient to disinfect the interior channel of the medical device and/or to disinfect human body substances in the patient's body may be performed for any exposure time. However, the exposure time may be, for example, greater than 4.0 minutes, such as between about 4.0 minutes and about 24 hours. The exposure time may be between about 30 minutes and about 12 hours, or even between about 1.0 hour and about 6.0 hours.

According to an aspect (1) of the present disclosure, a system for disinfecting a medical device is provided. The system comprises a light source that generates light having at least one wavelength between about 100 nm and about 500 nm; and at least one cylindrical optical diffuser disposed in optical communication with at least one interior channel of a medical device, the at least one cylindrical optical diffuser having an outer surface and an end optically coupled to the light source, wherein the at least one cylindrical optical diffuser is configured to scatter guided light through the outer surface to form a light diffuser portion having a length that emits substantially uniform radiation over its length.

According to another aspect (2) of the present disclosure, the system of aspect (1) is provided, wherein the cylindrical optical diffuser has a scattering-induced attenuation greater than about 50 dB km.

According to another aspect (3) of the present disclosure, the system of any of aspects (1)-(2) is provided, wherein the cylindrical optical diffuser radiation is substantially uniform, such that the difference between the minimum and maximum scattering illumination intensity is less than about 30% of the maximum scattering illumination intensity.

According to another aspect (4) of the present disclosure, the system of any of aspects (1)-(3) is provided, wherein the at least one cylindrical optical diffuser comprises a light diffusing optical fiber having a core, a primary cladding, and a plurality of nano-sized structures, and wherein the guided light is scattered through the outer surface via the nano-sized structures away from the core.

According to another aspect (5) of the present disclosure, the system of aspect (4) is provided, wherein the nano-sized structures are situated in the core.

According to another aspect (6) of the present disclosure, the system of any of aspects (4)-(5) is provided, wherein the nano-sized structures are gas filled voids having a diameter of greater than about 10 nm.

According to another aspect (7) of the present disclosure, the system of any of aspects (1)-(6) is provided, wherein an end of the at least one cylindrical optical diffuser opposite the end optically coupled to the light source is coated with a reflective coating.

According to another aspect (8) of the present disclosure, the system of any of aspects (1)-(7) is provided, wherein an end of the at least one cylindrical optical diffuser opposite the end optically coupled to the light source is coated with an absorptive coating.

According to another aspect (9) of the present disclosure, the system of any of aspects (1)-(8) is provided, wherein the at least one cylindrical optical diffuser comprises an outer coating, wherein the outer coating is a resin that transmits UV light.

According to another aspect (10) of the present disclosure, the system of aspect (9) is provided, wherein the resin that transmits UV light is selected from the group consisting of resins having structutes of tripropylene glycol diacrylate (TPGDA), polyester tetraacrylate, polyester hexaacrylate, aliphatic urethane diacrylate+hexanediol diacrylate, polyether tetraacrylate, silicone diacrylate, silicone hexaacrylate, epoxydiacrylate based on bisphenol A, and epoxydiacrylate based on bisphenol A+25% TPGDA.

According to another aspect (11) of the present disclosure, the system of any of aspects (1)-(10) is provided, wherein the light source generates light having at least one wavelength between about 100 nm and about 400 nm.

According to another aspect (12) of the present disclosure, the system of any of aspects (1)-(11) is provided, wherein the light source generates light having at least one wavelength between about 100 nm and about 290 nm.

According to another aspect (13) of the present disclosure, the system of any of aspects (1)-(10) is provided, wherein the light source generates light having at least one wavelength between about 400 nm and about 500 nm.

According to another aspect (14) of the present disclosure, a medical device is provided. The medical device comprises at least one interior channel, and at least one cylindrical optical diffuser disposed in optical communication with the least one interior channel, the at least one cylindrical optical diffuser having an outer surface and an end optically coupled to a light source, wherein the at least one cylindrical optical diffuser is configured to scatter guided light through the outer surface to form a light diffuser portion having a length that emits substantially uniform radiation over its length According to another aspect (15) of the present disclosure, the medical device of aspect (14) is provided, wherein the at least one cylindrical optical diffuser is disposed outside of the at least one interior channel.

According to another aspect (16) of the present disclosure, the medical device of aspect (14) is provided, wherein the at least one cylindrical optical diffuser is disposed inside of the at least one interior channel.

According to another aspect (17) of the present disclosure, the medical device of aspect (16) is provided, wherein the at least one cylindrical optical diffuser is partially disposed inside of the at least one interior channel.

According to another aspect (18) of the present disclosure, the medical device of any of aspects (14)-(17) is provided, wherein the at least one interior channel comprises a wall, wherein at least a portion of the wall comprises a material transmissive to light having at least one wavelength between about 100 nm and about 500 nm.

According to another aspect (19) of the present disclosure, the medical device of any of aspects (14)-(18) is provided, wherein the cylindrical optical diffuser has a scattering-induced attenuation greater than about 50 dB km.

According to another aspect (20) of the present disclosure, the medical device of any of aspects (14)-(19) is provided, wherein the cylindrical optical diffuser radiation is substantially uniform, such that the difference between the minimum and maximum scattering illumination intensity is less than about 30% of the maximum scattering illumination intensity.

According to another aspect (21) of the present disclosure, the medical device of any of aspects (14)-(20) is provided, wherein the at least one cylindrical optical diffuser comprises a light diffusing optical fiber having a core, a primary cladding, and a plurality of nano-sized structures, and wherein the guided light is scattered through the outer surface via the nano-sized structures away from the core.

According to another aspect (22) of the present disclosure, the medical device of aspect (21) is provided, wherein the nano-sized structures are situated in the core.

According to another aspect (23) of the present disclosure, the medical device of any of aspects (21)-(22) is provided, wherein the nano-sized structures are gas filled voids having a diameter of greater than about 10 nm.

According to another aspect (24) of the present disclosure, the medical device of any of aspects (14)-(23) is provided, wherein an end of the at least one cylindrical optical diffuser opposite the end optically coupled to the light source is coated with a reflective coating.

According to another aspect (25) of the present disclosure, the medical device of any of aspects (14)-(23) is provided, wherein an end of the at least one cylindrical optical diffuser opposite the end optically coupled to the light source is coated with an absorptive coating.

According to another aspect (26) of the present disclosure, the medical device of any of aspects (14)-(25) is provided, wherein the at least one cylindrical optical diffuser comprises an outer coating, wherein the outer coating is a resin that transmits UV light.

According to another aspect (27) of the present disclosure, the medical device of aspect (26) is provided, wherein the resin that transmits UV light is selected from the group consisting of resins having structutes of tripropylene glycol diacrylate (TPGDA), polyester tetraacrylate, polyester hexaacrylate, aliphatic urethane diacrylate+hexanediol diacrylate, polyether tetraacrylate, silicone diacrylate, silicone hexaacrylate, epoxydiacrylate based on bisphenol A, and epoxydiacrylate based on bisphenol A+25% TPGDA.

According to another aspect (28) of the present disclosure, the medical device of any of aspects (14)-(27) is provided, wherein the light source generates light having at least one wavelength between about 100 nm and about 500 nm.

According to another aspect (29) of the present disclosure, the medical device of any of aspects (14)-(28) is provided, wherein the light source generates light having at least one wavelength between about 100 nm and about 400 nm.

According to another aspect (30) of the present disclosure, the medical device of any of aspects (14)-(29) is provided, wherein the light source generates light having at least one wavelength between about 100 nm and about 290 nm.

According to another aspect (31) of the present disclosure, the medical device of any of aspects (14)-(28) is provided, wherein the light source generates light having at least one wavelength between about 400 nm and about 500 nm.

According to another aspect (32) of the present disclosure, a disinfection method is provided. The disinfection method comprises inserting at least a portion of at least one cylindrical optical diffuser into an interior channel of a medical device, and introducing light from a light source into an end of the at least one cylindrical optical diffuser optically coupled to the light source and emitting the light through the outer surface of the diffuser to illuminate a portion of the diffuser and to expose the interior channel to the emitted light, wherein the at least one cylindrical optical diffuser is configured to scatter guided light through the outer surface to form a light diffuser portion having a length that emits substantially uniform radiation over its length, and to disinfect at least one surface of the interior channel.

According to another aspect (33) of the present disclosure, the disinfection method of aspect (32) is provided, wherein the at least one cylindrical optical diffuser comprises a light diffusing optical fiber having a core, a primary cladding, and a plurality of nano-sized structures, and wherein the guided light is scattered through the outer surface via the nano-sized structures away from the core.

According to another aspect (34) of the present disclosure, the disinfection method of any of aspects (32)-(33) is provided, wherein introducing light from the light source is performed while at least a portion of the medical device is positioned in the body of a patient.

According to another aspect (35) of the present disclosure, the disinfection method of any of aspects (32)-(34) is provided, wherein the at least one cylindrical optical diffuser is configured to scatter guided light through the outer surface to disinfect human body substances.

According to another aspect (36) of the present disclosure, the disinfection method of aspect (35) is provided, wherein the human body substances are tissue within the body of the patient.

According to another aspect (37) of the present disclosure, the disinfection method of aspect (35) is provided, wherein the human body substances are fluids within the body of the patient.

According to another aspect (38) of the present disclosure, the disinfection method of any of aspects (32)-(37) is provided further comprising exposing the interior channel to a dose of light that is greater than about 5 mj/cm$^2$.

According to another aspect (39) of the present disclosure, the disinfection method of any of aspects (32)-(38) is provided further comprising exposing the interior channel to a dose of light that is between about 5 mj/cm$^2$ and about 175 mj/cm$^2$.

According to another aspect (40) of the present disclosure, the disinfection method of any of aspects (32)-(39) is provided further comprising exposing the interior channel to a dose of light that is between about 10 mj/cm$^2$ and about 150 mj/cm$^2$.

According to another aspect (41) of the present disclosure, the disinfection method of any of aspects (32)-(40) is provided further comprising exposing the interior channel to a dose of light that is between about 15 mj/cm$^2$ and about 80 mj/cm$^2$.

According to another aspect (42) of the present disclosure, the disinfection method of any of aspects (32)-(41) is provided, wherein introducing light from a light source comprises introducing light having at least one wavelength between about 100 nm and about 500 nm.

According to another aspect (43) of the present disclosure, the disinfection method of any of aspects (32)-(42) is provided, wherein introducing light from a light source comprises introducing light having at least one wavelength between about 100 nm and about 400 nm.

According to another aspect (44) of the present disclosure, the disinfection method of any of aspects (32)-(43) is provided, wherein introducing light from a light source comprises introducing light having at least one wavelength between about 100 nm and about 290 nm.

According to another aspect (45) of the present disclosure, the disinfection method of any of aspects (32)-(42) is provided, wherein introducing light from a light source comprises introducing light having at least one wavelength between about 400 nm and about 500 nm.

It will be apparent to those skilled in the art that various modifications and variations can be made without departing from the spirit or scope of the present disclosure.

What is claimed is:

1. A system for disinfecting a medical device, the system comprising:
    a light source that generates light; and
    at least one cylindrical optical diffuser disposed in optical communication with at least one interior channel of a medical device, the at least one cylindrical optical diffuser having an outer surface, and an end optically coupled to the light source, and a scattering-induced attenuation greater than about 50 dB/km, wherein the at least one cylindrical optical diffuser is configured to scatter guided light through the outer surface to transmit ultraviolet irradiation, or short wavelength visible light.

2. The system of claim 1, the at least one cylindrical optical diffuser forms a light diffuser portion having a length that emits substantially uniform radiation over its length such that the difference between the minimum and maximum scattering illumination intensity is less than about 30% of the maximum scattering illumination intensity.

3. The system of claim 1, wherein the at least one cylindrical optical diffuser comprises a light diffusing optical fiber having a core, a primary cladding, and a plurality of nano-sized structures, and wherein the guided light is scattered through the outer surface via the nano-sized structures away from the core.

4. The system of claim 3, wherein the nano-sized structures are situated in the core.

5. The system of claim 3, wherein the nano-sized structures are gas filled voids having a diameter of greater than about 10 nm.

6. The system of claim 1, wherein an end of the at least one cylindrical optical diffuser opposite the end optically coupled to the light source is coated with a reflective coating.

7. The system of claim 1, wherein an end of the at least one cylindrical optical diffuser opposite the end optically coupled to the light source is coated with an absorptive coating.

8. The system of claim 1, wherein the at least one cylindrical optical diffuser comprises an outer coating, wherein the outer coating is a resin that transmits UV light.

9. The system of claim 8, wherein the resin that transmits UV light is selected from the group consisting of resins having structutes of tripropylene glycol diacrylate (TPGDA), polyester tetraacrylate, polyester hexaacrylate, aliphatic urethane diacrylate+hexanediol diacrylate, polyether tetraacrylate, silicone diacrylate, silicone hexaacrylate, epoxydiacrylate based on bisphenol A, and epoxydiacrylate based on bisphenol A +25% TPGDA.

10. The system of claim 1, wherein the light source generates light having at least one wavelength between about 100 nm and about 400 nm.

11. The system of claim 1, wherein the light source generates light having at least one wavelength between about 400 nm and about 500 nm.

12. The system of claim 1, wherein ultraviolet irradiation comprises a wavelength of light less than about 400 nm, and short wavelength visible light comprises a wavelength of light in a range from about 400 nm to about 500 nm.

13. A medical device comprising:
at least one interior channel; and
at least one cylindrical optical diffuser disposed in optical communication with the least one interior channel, the at least one cylindrical optical diffuser having an outer surface, and an end optically coupled to a light source, and a scattering-induced attenuation greater than about 50 dB/km, wherein the at least one cylindrical optical diffuser is configured to scatter guided light through the outer surface to transmit ultraviolet irradiation, or short wavelength visible light.

14. The medical device of claim 13, wherein the at least one cylindrical optical diffuser is disposed outside of the at least one interior channel.

15. The medical device of claim 13, wherein the at least one cylindrical optical diffuser is disposed inside of the at least one interior channel.

16. The medical device of claim 15, wherein the at least one cylindrical optical diffuser is partially disposed inside of the at least one interior channel.

17. The medical device of claim 13, wherein the at least one interior channel comprises a wall, wherein at least a portion of the wall comprises a material transmissive to light having at least one wavelength between about 100 nm and about 500 nm.

18. The medical device of claim 13, wherein the cylindrical optical diffuser radiation is substantially uniform, such that the difference between the minimum and maximum scattering illumination intensity is less than about 30% of the maximum scattering illumination intensity.

19. The medical device of claim 13, wherein the at least one cylindrical optical diffuser comprises a light diffusing optical fiber having a core, a primary cladding, and a plurality of nano-sized structures, and wherein the guided light is scattered through the outer surface via the nano-sized structures away from the core.

20. The medical device of claim 19, wherein the nano-sized structures are situated in the core.

21. The medical device of claim 19, wherein the nano-sized structures are gas filled voids having a diameter of greater than about 10 nm.

22. The medical device of claim 13, wherein an end of the at least one cylindrical optical diffuser opposite the end optically coupled to the light source is coated with a reflective coating.

23. The medical device of claim 13, wherein an end of the at least one cylindrical optical diffuser opposite the end optically coupled to the light source is coated with an absorptive coating.

24. The medical device of claim 13, wherein the at least one cylindrical optical diffuser comprises an outer coating, wherein the outer coating is a resin that transmits UV light.

25. The medical device of claim 24, wherein the resin that transmits UV light is selected from the group consisting of resins having structutes of tripropylene glycol diacrylate (TPGDA), polyester tetraacrylate, polyester hexaacrylate, aliphatic urethane diacrylate+hexanediol diacrylate, polyether tetraacrylate, silicone diacrylate, silicone hexaacrylate, epoxydiacrylate based on bisphenol A, and epoxydiacrylate based on bisphenol A +25% TPGDA.

26. The medical device of claim 13, wherein the light source generates light having at least one wavelength between about 100 nm and about 500 nm.

27. The medical device of claim 13, wherein the light source generates light having at least one wavelength between about 400 nm and about 500 nm.

28. The medical device of claim 13, wherein ultraviolet irradiation comprises a wavelength of light less than about 400 nm, and short wavelength visible light comprises a wavelength of light in a range from about 400 nm to about 500 nm.

29. The medical device of claim 28, wherein the short wavelength visible light comprises a wavelength in a range from about 400 nm to about 450 nm, or from about about 405 nm to about 415 nm.

30. A disinfection method comprising:
  inserting at least a portion of at least one cylindrical optical diffuser into an interior channel of a medical device; and
  introducing light from a light source into an end of the at least one cylindrical optical diffuser optically coupled to the light source and emitting the light through the outer surface of the diffuser to illuminate a portion of the diffuser and to expose the interior channel to the emitted light,
  wherein the at least one cylindrical optical diffuser is configured to scatter guided light through the outer surface to transmit ultraviolet irradiation, or short wavelength visible light, and to disinfect at least one surface of the interior channel, and
  wherein the at least one cylindrical optical diffuser has a scattering-induced attenuation greater than about 50 dB/km.

31. The method of claim 30, wherein the at least one cylindrical optical diffuser comprises a light diffusing optical fiber having a core, a primary cladding, and a plurality of nano-sized structures, and wherein the guided light is scattered through the outer surface via the nano-sized structures away from the core.

32. The method of claim 30, wherein the at least one cylindrical optical diffuser is configured to scatter guided light through the outer surface to disinfect human body substances.

33. The method of claim 30, further comprising exposing the interior channel to a dose of light that is greater than about 5 mj/cm$^2$.

34. The method of claim 30, further comprising exposing the interior channel to a dose of light that is between about 5 mj/cm$^2$ and about 175 mj/cm$^2$.

35. The method of claim 30, further comprising exposing the interior channel to a dose of light that is between about 10 mj/cm$^2$ and about 150 mj/cm$^2$.

36. The method of claim 30, further comprising exposing the interior channel to a dose of light that is between about 15 mj/cm$^2$ and about 80 mj/cm$^2$.

37. The method of claim 30, wherein introducing light from a light source comprises introducing light having at least one wavelength between about 100 nm and about 500 nm.

38. The method of claim 30, wherein ultraviolet irradiation comprises a wavelength of light less than about 400 nm, and short wavelength visible light comprises a wavelength of light in a range from about 400 nm to about 500 nm.

39. The method of claim 38, wherein the short wavelength visible light comprises a wavelength in a range from about 400 nm to about 450 nm, or from about 405 nm to about 415 nm.

* * * * *

UNITED STATES PATENT AND TRADEMARK OFFICE
CERTIFICATE OF CORRECTION

| | | |
|---|---|---|
| PATENT NO. | : 10,856,952 B2 | Page 1 of 1 |
| APPLICATION NO. | : 16/715327 | |
| DATED | : December 8, 2020 | |
| INVENTOR(S) | : Anthony Sebastian Bauco et al. | |

It is certified that error appears in the above-identified patent and that said Letters Patent is hereby corrected as shown below:

On the Title Page

On page 2, in Column 2, item (56), Other Publications, Line 8, delete "Brochoscopy" and insert -- Bronchoscopy --, therefor.

In the Claims

In Column 23, Line 8, Claim 2, after "claim 1," insert -- wherein --.

In Column 23, Line 40, Claim 9, delete "structutes" and insert -- structures --, therefor.

In Column 24, Line 46, Claim 25, delete "structutes" and insert -- structures --, therefor.

In Column 24, Line 66, Claim 29, after "or from" delete "about".

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*